US012718613B2

(12) United States Patent
Garcia et al.

(10) Patent No.: US 12,718,613 B2
(45) Date of Patent: Aug. 25, 2026

(54) APPROACHES TO ESTIMATING HAND POSE WITH INDEPENDENT DETECTION OF HAND PRESENCE IN DIGITAL IMAGES OF INDIVIDUALS PERFORMING PHYSICAL ACTIVITIES AND SYSTEMS FOR IMPLEMENTING THE SAME

(71) Applicant: Hinge Health, Inc., San Francisco, CA (US)

(72) Inventors: Abel Gonzalez Garcia, Montreal (CA); Colin Joseph Brown, Saskatoon (CA)

(73) Assignee: Hinge Health, Inc., San Francisco, CA (US)

( * ) Notice: Subject to any disclaimer, the term of this patent is extended or adjusted under 35 U.S.C. 154(b) by 191 days.

(21) Appl. No.: 18/365,878

(22) Filed: Aug. 4, 2023

(65) Prior Publication Data

US 2024/0046690 A1 Feb. 8, 2024

Related U.S. Application Data

(60) Provisional application No. 63/370,467, filed on Aug. 4, 2022.

(51) Int. Cl.
*G06V 40/10* (2022.01)
*G06T 7/11* (2017.01)
(Continued)

(52) U.S. Cl.
CPC ................ *G06V 40/11* (2022.01); *G06T 7/11* (2017.01); *G06T 7/70* (2017.01); *G06T 7/73* (2017.01);
(Continued)

(58) Field of Classification Search
CPC ........ G06V 40/11; G06V 10/25; G06V 10/56; G06V 10/771; G06V 2201/07;
(Continued)

(56) References Cited

U.S. PATENT DOCUMENTS

| | | | | |
|---|---|---|---|---|
| 10,956,724 | B1 * | 3/2021 | Terrano | G06V 10/82 |
| 11,854,308 | B1 * | 12/2023 | Marsden | G06V 10/454 |

(Continued)

FOREIGN PATENT DOCUMENTS

WO 2020056391 A1 3/2020

OTHER PUBLICATIONS

International Search Report and Written Opinion mailed on Dec. 5, 2023 for International Patent Application No. PCT/IB2023/057932, 8 pages.

*Primary Examiner* — Vincent Rudolph
(74) *Attorney, Agent, or Firm* — Ashurst Perkins Coie US LLP; Andrew T. Pettit

(57) ABSTRACT

Introduced here are computer-implemented platforms (also referred to as "pose monitoring platforms") that are designed to improve adherence to, and success of, programs requiring performance of physical activities. As part of a program, a participant may be requested to engage with a pose monitoring platform to perform a single physical activity, multiple repetitions of a single physical activity, or multiple repetitions of multiple physical activities. The pose monitoring platform can determine, for example, using a neural network that has parallel branches, whether digital images of the participant's environment includes certain body parts and then estimate poses of those body parts. The pose monitoring platform can use the estimated poses to guide the participant through the program, such as by providing instructions for performing the physical activities.

13 Claims, 9 Drawing Sheets

(51) Int. Cl.

| | |
|---|---|
| ***G06T 7/70*** | (2017.01) |
| ***G06T 7/73*** | (2017.01) |
| ***G06V 10/25*** | (2022.01) |
| ***G06V 10/56*** | (2022.01) |
| ***G06V 10/771*** | (2022.01) |
| ***G09B 5/02*** | (2006.01) |
| ***G16H 20/30*** | (2018.01) |

(52) U.S. Cl.
CPC .............. *G06V 10/25* (2022.01); *G06V 10/56* (2022.01); *G06V 10/771* (2022.01); *G09B 5/02* (2013.01); *G16H 20/30* (2018.01); *G06T 2200/24* (2013.01); *G06T 2207/20081* (2013.01); *G06T 2207/20084* (2013.01); *G06T 2207/30196* (2013.01); *G06V 2201/07* (2022.01)

(58) Field of Classification Search
CPC ...... G06V 40/103; G06V 40/23; G06V 10/82; G06T 7/11; G06T 7/70; G06T 7/73; G06T 2200/24; G06T 2207/20081; G06T 2207/20084; G06T 2207/30196; G09B 5/02; G16H 20/30
See application file for complete search history.

(56) References Cited

U.S. PATENT DOCUMENTS

| | | | | |
|---|---|---|---|---|
| 2010/0125026 | A1* | 5/2010 | Zavadsky | A63F 9/24 482/5 |
| 2013/0057713 | A1 | 3/2013 | Khawand | |
| 2014/0232863 | A1 | 8/2014 | Paliga et al. | |
| 2016/0099010 | A1 | 4/2016 | Sainath et al. | |
| 2017/0076142 | A1* | 3/2017 | Chang | G06T 7/11 |
| 2019/0143517 | A1* | 5/2019 | Yang | G06N 5/046 700/245 |
| 2019/0188533 | A1 | 6/2019 | Katabi et al. | |
| 2019/0362139 | A1 | 11/2019 | Mehl et al. | |
| 2020/0090408 | A1* | 3/2020 | Virkar | G06V 10/764 |
| 2020/0272888 | A1 | 8/2020 | Wang et al. | |
| 2020/0401851 | A1 | 12/2020 | Mau et al. | |
| 2021/0191519 | A1* | 6/2021 | Zhao | G06N 3/09 |
| 2021/0192197 | A1* | 6/2021 | Zhao | G06V 10/25 |
| 2021/0233273 | A1 | 7/2021 | Spurr et al. | |
| 2022/0351547 | A1* | 11/2022 | Zhou | G06F 3/017 |
| 2023/0334299 | A1* | 10/2023 | Jain | G06N 3/094 |
| 2023/0350499 | A1* | 11/2023 | Lu | G06F 3/017 |

* cited by examiner

APPROACHES TO ESTIMATING HAND POSE WITH INDEPENDENT DETECTION OF HAND PRESENCE IN DIGITAL IMAGES OF INDIVIDUALS PERFORMING PHYSICAL ACTIVITIES AND SYSTEMS FOR IMPLEMENTING THE SAME

CROSS-REFERENCE TO RELATED APPLICATIONS

This application claims priority to U.S. Provisional Application No. 63/370,467, titled "Hand Presence Detection for Hand Pose Estimation" and filed on Aug. 4, 2022, which is incorporated herein by reference in its entirety.

TECHNICAL FIELD

Various embodiments concern computer programs designed to detect the spatial location and orientation of various body parts and associated systems and methods.

BACKGROUND

Exercise therapy is an intervention technique that utilizes physical activity as the principal treatment method for addressing the symptoms of musculoskeletal ("MSK") conditions, such as acute physical ailments and chronic physical ailments. Exercise therapy programs may involve a plan for performing physical activities during exercise therapy sessions that occur on a periodic basis. Generally, the purpose of an exercise therapy program is to either restore normal MSK function or reduce the pain caused by an acute physical ailment or chronic physical ailment. As such, the physical activities to be performed in each exercise therapy session may be selected in order to achieve a specific therapeutic goal. Examples of therapeutic goals include lessening pain, improving flexibility, rehabilitating injuries, managing diseases, and the like.

These exercise therapy programs normally depict how an individual (also called a "participant" or "user") should perform one or more physical activities to achieve a specific therapeutic goal within a time period. However, these exercise therapy programs usually are unable to monitor whether the participant is properly performing the physical activities. For example, if the participant is not using the proper technique to perform a physical activity, she may not experience improvement in pain or flexibility, resulting in the participant becoming discouraged from completing further exercise therapy sessions. Therefore, a better approach is needed for monitoring pose to ensure that participants are able to achieve lasting improvement in terms of MSK function. The benefits of improved performance of poses are not limited to exercise therapy programs.

Other systems that guide, provoke, or otherwise facilitate training of participants to perform physical activities may also be unable to monitor whether a participant is properly performing a variety of physical activities, such as dance moves, sporting techniques, exercises, cooking techniques, and the like. For example, if a participant is not using proper form for her forehands, she may not be as successful in tennis matches compared to if she were using proper form. In another example, a participant may be penalized in a cooking competition for not cutting her vegetables in a specific manner, and a system could have informed her—thereby teaching her proper cutting technique—with the ability to monitor her cutting technique. Thus, these systems need a way to monitor physical activities for participants to achieve improved form.

Figure 1:
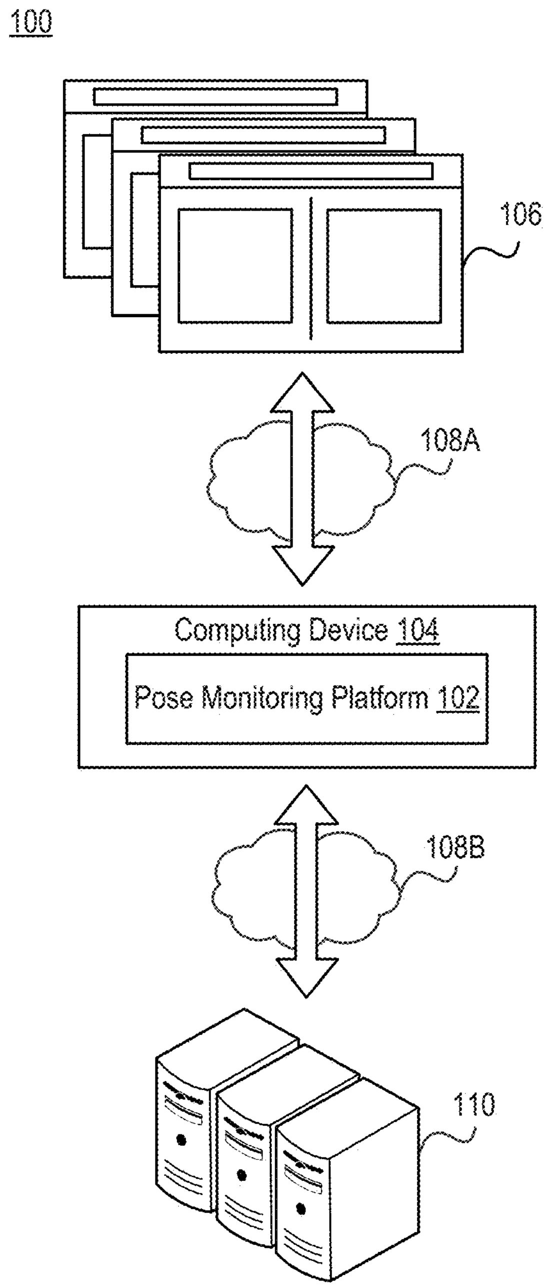
FIG. 1 illustrates an example of a network environment that includes a pose monitoring platform that is executed by a computing device.

Various features of the technology described herein will become more apparent to those skilled in the art from a study of the Detailed Description in conjunction with the drawings. Various embodiments are depicted in the drawings for the purpose of illustration. However, those skilled in the art will recognize that alternative embodiments may be employed without departing from the principles of the technology. Accordingly, although specific embodiments are shown in the drawings, the technology is amenable to various modifications.

DETAILED DESCRIPTION

Introduced here are computer-implemented platforms that are designed to improve adherence to, and success of, care programs that are assigned to participants for completion. A care program (or simply "program") may be designed for one or more MSK conditions. As an example, a program may be designed in an effort to address (e.g., alleviate or lessen) the pain that tends to accompany a given MSK condition, as well as facilitate the continued engagement that is critical for long-term success. Specifically, the program may instruct, prompt, or otherwise elicit performance of physical activities that are meant to improve different aspects of the given MSK condition. Examples of physical activities include exercises, stretches, and the like.

As part of a program, a participant may be requested to engage with a computer-implemented platform (also referred to as a "motion monitoring platform" or "pose monitoring platform") that is accessible via a computer program executing on a computing device. The term "participant" may be used to generally refer to an individual who engages in physical activities that are monitored by the pose monitoring platform. Over time, the participant may be instructed to perform physical activities during physical activity sessions (or simply "sessions") as part of a program.

For example, the participant may be instructed to perform a series of physical activities over the course of a session, and the participant may be prompted to complete a series of sessions over the course of several days, weeks, or months. The pose monitoring platform may not only assist the participant by actively guiding her through each session, but also help her achieve and maintain proper technique in performing the physical activities.

As further discussed below, a pose monitoring platform may represent one part of the physical activity computing system (or simply "computing system" or "system") that is designed to promote compliance with a program by estimating the poses of participants via computer vision techniques as those participants perform physical activities. Though embodiments may be described in relation to physical activities (e.g., exercises)—the performance of which is intended to have a therapeutic effect—the pose monitoring platform may be used to monitor performances of physical activities for purposes beyond healthcare, such as for wellness, sports, dance, virtual reality, augmented reality, cooking, art, or any other endeavor that requires physical activities be performed in a particular manner (or simply benefits from physical activities being performed in a particular manner). More detailed examples of how monitoring pose can be helpful in different contexts are provided below.

Significant advances have been made in the field of computer vision over the last several years. This has resulted in the development of sophisticated pose estimation programs (also called "pose estimators" or "pose predictors") that are designed to perform pose estimation, generally through the analysis of pixels in an image. Pose estimation has historically been performed in a top-down manner: one or more parts of a living body are detected in an image, cropped out, and processed by the pose estimator. Given the overhead of a dedicated body part detector, a pose estimator may generate bounding boxes heuristically (e.g., by using the location of detected keypoints corresponding to anatomical regions of interest). Such heuristic-based pose estimators are prone to errors under challenging conditions, such as motion blur, body part occlusion, and the like, which result in suboptimal detections that often do not contain an actual instance of a body part. On the other hand, some pose estimators tend to hallucinate keypoints (e.g., by detecting body parts where none are present) on skin-colored portions of image, such as those on other participant's bodies. To alleviate the effect of hallucinated keypoints, the pose monitoring platform described herein can use a secondary branch in a pose estimation model to predict body part presence in a cropped segment of an image provided as input. As further discussed below, the pose estimation model employed by the pose monitoring platform may be representative of a neural network or other type of machine learning model. If the prediction is negative, the accuracy of the pose estimation by the pose estimation model is not compromised as the pose estimation model can disregard the hallucinated keypoints.

For multi-task learning, additional branches may be added to the pose estimation model to perform parallel tasks. Moreover, the addition of a lightweight branch leveraging intermediate features does not excessively impact runtime performance of the pose estimation model. Regarding the pose estimation model described herein, experiments using the pose estimation model have proven that the pose estimation model can predict presence or absence of body parts based on intermediate features and joint heatmaps employed for two-dimensional body part pose estimation. By exclusively training the secondary branch, the addition of the secondary branch does not alter the accuracy of the original pose estimation model, and the training of the secondary branch may be carried out once the rest of the pose estimation model is fully trained. The high accuracy values offered by the pose estimation model can effectively reduce the number of wrong poses output by the pose monitoring platform.

An alternative to the pose monitoring platform described herein is employing a pose estimator with a built-in presence score that indicates whether an object or body part is depicted in an image. However, such pose estimators may result be too computationally demanding for some applications, especially those that involve parallel processing of various tasks (e.g., detecting body parts and detecting objects other than body parts). Heuristic-based pose estimators that are computationally "lightweight," or even motion tracking programs (also called "trackers") that estimate location of a body part based on its previous location, do not generally provide a presence score. Another alternative would be to use confidence of the estimated keypoints to determine presence likelihood, but this alternative is sometimes not a reliable signal given that some machine learning models—like neural networks—tend to overestimate the confidence of detections. This issue is apparent by the large number of confidently detected, yet hallucinated, keypoints in experiments with images that do not contain body parts. One more alternative would be to use active learning to more reliably estimate the confidence of predictions of the pose estimation model, but this approach tends to be computationally expensive and not as reliable or explicit as having a dedicated branch of the pose estimation model to predict body part presence.

Generally, the pose monitoring platform described herein is embodied as a computer program executing on a computing device that is accessible to a participant. This computing device may be coupled to one or more image sensors that capture data about the environment surrounding a participant. As the participant completes physical activities during a session, the computing device can send image data captured by these image sensors to the pose monitoring platform for computer vision analysis. By analyzing this image data, the pose monitoring platform may be able to establish whether the participant is performing the physical activities as requested (e.g., by determining poses of body parts). This approach is computationally lightweight and can be applied on a previously cropped image patch, which only marginally increases the total runtime of the pose estimation model compared to a machine learning model that does not employ a secondary branch. Moreover, the approach is dedicated to determining body part presence or absence, and therefore provides a complementary signal to keypoint detection confidence. Such an approach enables the pose monitoring platform to provide personalized feedback to a participant about the physical activities that the participant has performed. Moreover, the pose monitoring platform may tailor a program (or individual sessions) based on its knowledge of participant movement. For example, if the pose monitoring platform determines that a participant struggled to perform a physical activity (e.g., based on determined body poses), then the pose monitoring platform may issue further instructions to the participant of how to properly perform the physical activity. At a high level, the pose monitoring platform is representative of a pathway for digitally engaging participants in a consistent, meaningful way.

As further discussed below, other avenues of communication may be employed as well. For example, a coach may be able to interact directly with participants (e.g., via text messages, email, video, etc.) in addition to communicating with those participants through the pose monitoring platform. The term "coach" may be used to generally refer to individuals who prompt, encourage, or otherwise facilitate engagement by participants with programs. Similarly, participants could be connected with healthcare professionals such as physical therapists, physicians, nurses, counselors, etc. For example, the pose monitoring platform may generate interfaces through which a coach can serve as a guide, partner, or "cheerleader" for a participant as she completes sessions in accordance with a program. Similarly, the pose monitoring platform may generate interfaces through which a healthcare professional can obtain or rely on advice regarding symptoms, treatment, and the like.

As mentioned above, the approaches introduced here for estimating pose could be used across different applications. Accordingly, while embodiments may be described in the context of healthcare, features of those embodiments may be similarly applicable to other fields related to performing physical activities. Similarly, while embodiments may be described in the context of "coaches," features of those embodiments may be similarly applicable to other professionals. In addition to, or instead of, facilitating communication with coaches and healthcare professions, the pose monitoring platform could facilitate communication with athletes, athletics coaches, dance instructors, chefs, cooking instructors, art instructors, and the like.

For the purpose of illustration, embodiments may be described with reference to particular anatomical regions, sensor data analysis techniques, pose applications (e.g., dance, therapy, sports, etc.), and the like. However, those skilled in the art will recognize that the features are similarly applicable to other anatomical regions, computer vision techniques, and use cases. As an example, while embodiments may be described in the context of an image sensor that captures image data about the environment around a participant, the features described herein may be applied by a physical activity system having any number of image sensors arranged throughout the environment. In fact, a pose monitoring platform may establish the spatial position of different anatomical regions over time and then determine whether those spatial positions indicate that the physical activities were performed properly. For example, an image sensor that is embedded in a computing device (e.g., a mobile phone or tablet computer) may be used for capturing image data of a participant playing a virtual reality game, or an image sensor may be affixed to the top of a television for capturing image data of a participant playing a virtual reality game. The pose monitoring platform may be able to infer whether the participant dodged monsters in the virtual reality game based on the image data captured by the image sensor. In another example, two image sensors may be placed in a kitchen, one above the island and the other above the stove. The pose monitoring platform may use image data of a participant's hands captured by either image sensor to determine if a participant is using proper technique when chopping and sauteing zucchini. The pose monitoring platform may employ any number of computer vision techniques for determining body poses in these scenarios. Examples of computer vision techniques include image classification, object detection, object tracking, semantic segmentation, and instance segmentation.

Moreover, embodiments may be described in the context of computer-executable instructions for the purpose of illustration. However, aspects of the technology can be implemented via hardware or firmware in addition to, or instead of, software. As an example, a pose monitoring platform may be embodied as a computer program that offers support for completing sessions as part of a program, enables communication between participants and coaches, and determines which physical activities are appropriate for a session given past performance, specified preferences, etc.

Terminology

References in the present disclosure to "an embodiment" or "some embodiments" mean that the feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the terms "comprise," "comprising," and "comprised of" are to be construed in an inclusive sense rather than an exclusive or exhaustive sense. That is, in the sense of "including but not limited to."

The term "based on" is also to be construed in an inclusive sense. Thus, the term "based on" is intended to mean "based at least in part on."

The terms "connected," "coupled," and variants thereof are intended to include any connection or coupling between two or more elements, either direct or indirect. The connection or coupling can be physical, logical, or a combination thereof. For example, elements may be electrically or communicatively coupled to one another despite not sharing a physical connection.

The term "module" may refer broadly to software, firmware, hardware, or combinations thereof. Modules are typically functional components that generate one or more outputs based on one or more inputs. A computer program may include or utilize one or more modules. For example, a computer program may utilize multiple modules that are responsible for completing different tasks, or a computer program may utilize a single module that is responsible for completing all tasks.

When used in reference to a list of multiple items, the word "or" is intended to cover all of the following interpretations: any of the items in the list, all of the items in the list, and any combination of items in the list.

Overview of Pose Monitoring Platform

As discussed above, a pose monitoring platform may be responsible for guiding a participant through sessions that are performed as part of a program. As part of the program, the participant may be requested to engage with the pose monitoring platform on a periodic basis, and the pose monitoring platform may be responsible for monitoring the pose of the participant through analysis of digital images (or simply "images") that contain her and are captured as she completes a physical activity. The frequency with which the participant is requested to engage with the pose monitoring platform may be based on factors such as the anatomical region for which therapy is needed, the MSK condition (or non-healthcare related condition, such as desire to improve technique) for which therapy is needed, the difficulty of the program, the age of the participant, the amount of progress that has been achieved, and the like.

The pose monitoring platform may perform two-dimensional ("2D") pose estimation, where a pose comprises 2D locations of anatomical landmarks in an image, or three-dimensional ("3D") pose estimation, where a pose comprises 3D locations of anatomical landmarks in an image.

Examples of anatomical landmarks include joints (e.g., elbows, shoulders, knees), body parts (e.g., left hand, right hand, left shin, right foot, etc.), and body regions (e.g., abdominal region, cranial region, facial region). For accuracy, the pose monitoring platform can perform pose estimation in a top-down manner by detecting body part instances in an image, cropping the body part instances out of the image, and processing the crops using a pose estimation model. The pose estimation model may be trained on images of body parts, so without a branch to determine whether an image includes a body part, the pose estimation model may "hallucinate" by assuming that each image includes a body part and outputting an estimated pose even if the image does not contain a body part. To alleviate this hallucination effect, the pose estimation model can include a first branch for predicting body part presence along with a second branch for estimating pose. The first branch provides an added layer of prediction to the pose estimation model and outputs higher scores for an image that includes a body part than for an image that does not.

As mentioned above, the pose monitoring platform may estimate pose in contexts that are unrelated to healthcare, for example, to improve technique. For example, the pose monitoring platform may estimate pose of an individual while she completes an athletic activity (e.g., dancing, shooting a basketball, throwing a baseball), a virtual reality activity, an augmented reality activity, a cooking activity, an art activity, etc. Accordingly, while embodiments may be described in the context of a "participant," the features of those embodiments may be similarly applicable to individuals performing physical activities. These individuals may also be referred to as "actors" or "users" of the pose monitoring platform.

Even if the pose monitoring platform is able to request that a participant engage at a given frequency, the participant will normally have the autonomy to engage with the program as frequently as she desires. Thus, the participant may define a schedule for completing sessions (e.g., every day, every other day, or twice per week) as further discussed below, and various features of the pose monitoring platform may be designed in support of this habit formation. Alternatively, the participant may complete sessions on an ad hoc basis.

FIG. 1 illustrates a network environment 100 that includes a pose monitoring platform 102 that is executed by a computing device 104. Individuals can interact with the pose monitoring platform 102 via interfaces 106 as further discussed below. For example, participants may be able to access interfaces that are designed to guide them through sessions, present educational content, indicate progress, present feedback, etc. As another example, coaches may be able to access interfaces through which information regarding completed physical activities can be reviewed, feedback can be provided, etc. Thus, interfaces 106 generated by the pose monitoring platform 102 may serve as informative spaces for participants or coaches, or the interfaces 106 generated by the pose monitoring platform 102 may serve as collaborative spaces through which participants and coaches can communicate with one another.

As shown in FIG. 1, the pose monitoring platform 102 may reside in a network environment 100. Thus, the computing device 104 on which the pose monitoring platform 102 is executing may be connected to one or more networks 108A-B. Depending on its nature, the computing device 104 could be connected to a personal area network ("PAN"), local area network ("LAN"), wide area network ("WAN"), metropolitan area network ("MAN"), or cellular network. For example, if the computing device 104 is a mobile phone, then the computing device 104 may be connected to a computer server of a server system 110 via the Internet. As another example, if the computing device 104 is a computer server, then the computing device 104 may be accessible to users via respective computing devices that are connected to the Internet via LANs.

The interfaces 106 may be accessible via a web browser, desktop application, mobile application, or another form of computer program. For example, to interact with the pose monitoring platform 102, a coach may initiate a web browser on the computing device 104 and then navigate to a web address associated with the pose monitoring platform 102. Through the web browser, the coach may be able to review the progress of participants, communicate with participants, or personalize participants' sessions (e.g., based on their needs and past progress). As another example, a particular may access, via a desktop application or mobile application, interfaces that are generated by the motion monitoring platform 102 through which she can select physical activities to complete, review analyses of her performance of the physical activities, and the like. Accordingly, interfaces generated by the motion monitoring platform 102 may be accessible via various computing devices, including mobile phones, tablet computers, desktop computers, wearable electronic devices (e.g., watches or fitness accessories), mobile workstations (also called "computer carts"), virtual reality systems, augmented reality systems, and the like.

Generally, the pose monitoring platform 102 is hosted, at least partially, on the computing device 104 that is responsible for generating the images to be analyzed, as further discussed below. For example, the pose monitoring platform 102 may be embodied as a mobile application executing on a mobile phone or tablet computer. In such embodiments, the instructions that, when executed, implement the pose monitoring platform 102 may reside largely or entirely on the mobile phone or tablet computer. Note, however, that the mobile application may be able to access a server system 110 on which other aspects of the pose monitoring platform 102 are hosted.

In some embodiments, aspects of the pose monitoring platform 102 are executed by a cloud computing service operated by, for example, Amazon Web Services®, Google Cloud Platform™, or Microsoft Azure®. Accordingly, the computing device 104 may be representative of a computer server that is part of a server system 110. Often, the server system 110 is comprised of multiple computer servers that are accessible via a network (e.g., the Internet). These computer servers can include information regarding different programs, sessions, or physical activities; computer-implemented templates (or simply "templates") that indicate how anatomical landmarks should move when a given physical activity is performed; algorithms for processing data from which spatial position or orientation of anatomical regions can be computed, inferred, or otherwise determined; participant data such as name, age, weight, ailment, enrolled program, duration of enrollment, number of sessions completed, and number of physician activities completed; and other assets.

Those skilled in the art will recognize that this information could also be distributed amongst the server system 110 and one or more computing devices. For example, some participant data may be stored on, and processed by, her own computing device for security and privacy purposes. This participant data may be processed (e.g., encrypted or obfuscated) before being transmitted to the server system 110. As another example, some participant data may be retrieved from an electronic health record (also called an "electronic medical record") that is maintained for the participant. Electronic health records are normally maintained in storage that is managed by, or at least accessible to, healthcare systems, and this storage may be accessible to the pose monitoring platform 102 (e.g., via an application programming interface). As another example, the heuristics, algorithms, and models needed to process image data to establish the spatial position or spatial orientation of anatomical landmarks of a given individual can be computed, inferred, or otherwise determined may be stored on, or accessible to, a computing device associated with the given individual to ensure that such image data can be processed in real time (e.g., as physical activities are performed as part of a session). In some embodiments, the pose monitoring platform 102 is able to establish the spatial position or spatial orientations of anatomical landmarks through analysis of data that is generated by one or more sensor units that are secured to the participant (e.g., proximate to the anatomical landmarks). This sensor data could be analyzed in addition to, or instead of, image data that is representative of one or more images of the participant.

Figure 2A:
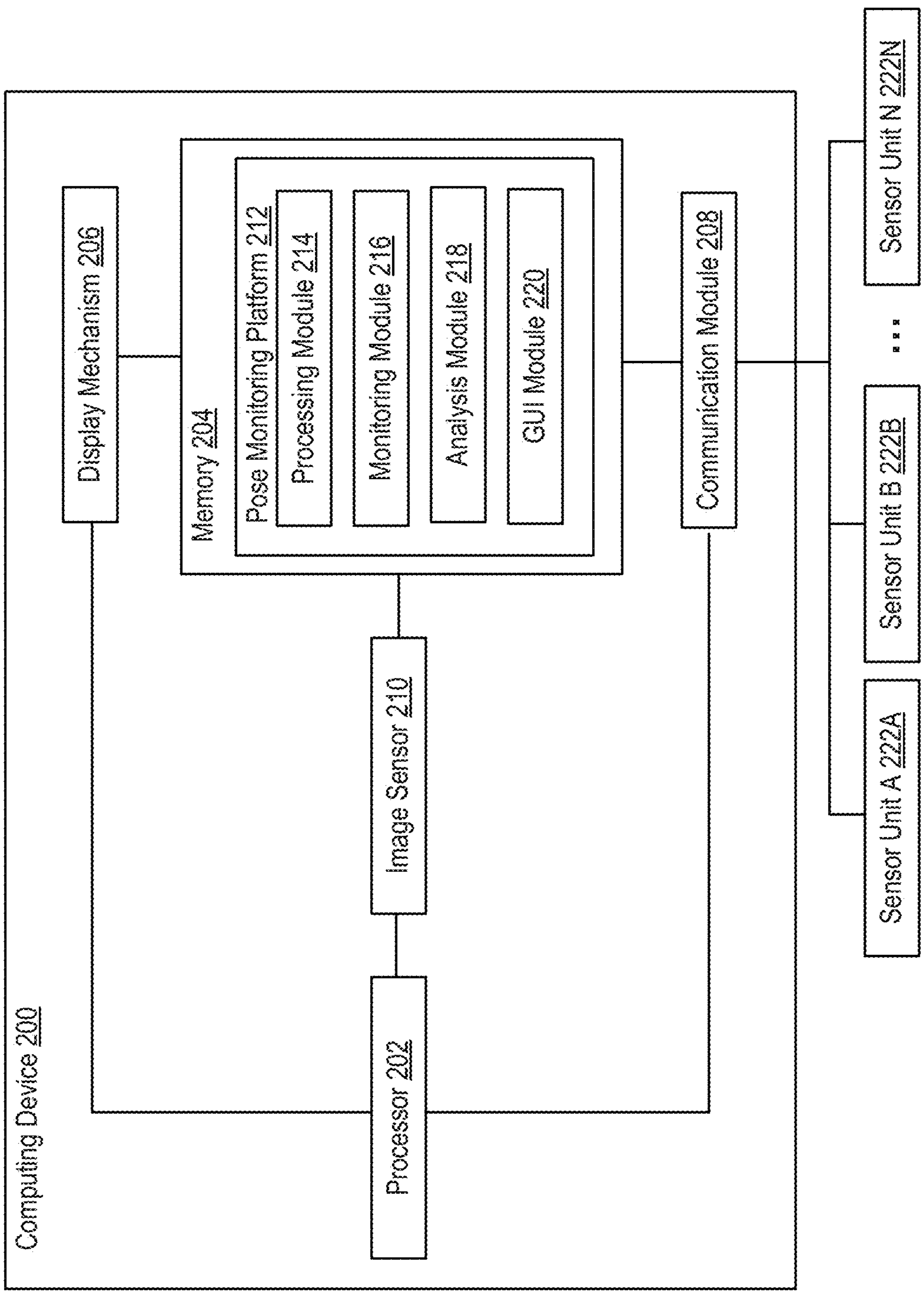
FIG. 2A illustrates an example of a computing device able to implement a program in which a participant is requested to perform physical activities, such as exercises, during sessions by a pose monitoring platform.

FIG. 2A illustrates an example of a computing device 200 that is able to implement a program in which a participant is requested to perform physical activities, such as exercises, during sessions and those performances are analyzed by a pose monitoring platform 212. In some embodiments, the pose monitoring platform 212 is embodied as a computer program that resides in memory 204 and is executed by a processor 202 as shown in FIG. 2A. In other embodiments, the pose monitoring platform 212 is embodied as a computer program that is executed by another computing device (e.g., a computer server that is part of server system 110 of FIG. 1) to which the computing device 200 is communicatively connected. In such embodiments, the computing device 200 may transmit image data generated by the image sensor 210 to the other computing device for processing. Those skilled in the art will recognize that aspects of the computer program could also be distributed amongst multiple computing devices.

As shown in FIG. 2A, the computing device 200 can include a processor 202, memory 204, display mechanism 206, communication module 208, and image sensor 210. Each of these components is discussed in greater detail below. Each of these components is discussed in greater detail below.

Those skilled in the art will recognize that different combinations of these components may be present depending on the nature of the computing device 200. For example, if the computing device 200 is a computer server that is part of a server system (e.g., server system 110 of FIG. 1), then the computing device 200 may not include the display mechanism 206 or image sensor 210, though the computing device 200 may be communicatively connectable to another computing device that does include a display mechanism and/or an image sensor.

The processor 202 can have generic characteristics similar to general-purpose processors, or the processor 202 may be an application-specific integrated circuit ("ASIC") that provides control functions to the computing device 200. As shown in FIG. 2A, the processor 202 can be coupled to all components of the computing device 200, either directly or indirectly, for communication purposes.

The memory 204 may be comprised of any suitable type of storage medium, such as static random-access memory ("SRAM"), dynamic random-access memory ("DRAM"), electrically erasable programmable read-only memory ("EEPROM"), flash memory, or registers. In addition to storing instructions that can be executed by the processor 202, the memory 204 can also store data generated by the processor 202 (e.g., when executing the modules of the pose monitoring platform 212) and produced, retrieved, or obtained by the other components of the computing device 200. For example, image data generated by the image sensor 210 may be stored in the memory 204, or sensor data received by the communication module 208 from the sensor units 222A-N may be stored in the memory 204. As mentioned above, image data could also be obtained from a source external to the computing device 200—like an external camera peripheral, such as a video camera or webcam—in which case the image data may be received by the communication module 208 and stored in the memory 204. Note that the memory 204 is merely an abstract representation of a storage environment. The memory 204 could be comprised of actual memory integrated circuits (also referred to as "chips").

The display mechanism 206 can be any mechanism that is operable to visually convey information. For example, the display mechanism 206 may be a panel that includes light-emitting diodes ("LEDs"), organic LEDs, liquid crystal elements, or electrophoretic elements. In some embodiments, the display mechanism 206 is touch sensitive. Thus, a participant may be able to provide input to the pose monitoring platform 212 by interacting with the display mechanism 206. Alternatively, the participant may be able to provide input to the pose monitoring platform 212 through some other control mechanism.

The communication module 208 may be responsible for managing communications external to the computing device 200. For example, the communication module 208 may be responsible for managing communications with other computing devices (e.g., server system 110 of FIG. 1 or a camera peripheral). The communication module 208 may be wireless communication circuitry that is designed to establish communication channels with other computing devices. Examples of wireless communication circuitry include 2.4 gigahertz ("GHz") and 5 GHz chipsets compatible with Institute of Electrical and Electronics Engineers ("IEEE") 802.11—also referred to as "Wi-Fi chipsets." Alternatively, the communication module 208 may be representative of a chipset configured for Bluetooth®, Near Field Communication ("NFC"), and the like. Some computing devices—like mobile phones and tablet computers—are able to wirelessly communicate via separate channels. Accordingly, the communication module 208 may be one of multiple communication modules implemented in the computing device 200. As an example, the communication module 208 may initiate and then maintain one communication channel with a camera peripheral (e.g., via Bluetooth) or sensor units 220A-N, and the communication module 208 may initiate and then maintain another communication channel with a server system (e.g., via the Internet).

The nature, number, and type of communication channels established by the computing device 200—and more specifically, the communication module 208—may depend on the sources from which data is received by the pose monitoring platform 212 and the destinations to which data is transmitted by the pose monitoring platform 212. Assume, for example, that the computing device 200 is representative of a mobile phone or tablet computer that is associated with (e.g., owned by) a participant. In some embodiments the communication module 208 may only externally communicate with a computer server, while in other embodiments the communication module 208 may also externally communicate with a source from which to receive image data. The source could be another computing device (e.g., a mobile phone or camera peripheral that includes an image sensor) to which the mobile device is communicatively connected. Image data could be received from the source even if the mobile phone generates its own image data. Thus, image data could be acquired from multiple sources, and these image data may correspond to different perspectives of the participant performing a physical activity. Regardless of the number of sources, image data—or analyses of the image data—may be transmitted to the computer server for storage in a digital profile that is associated with the participant. The same may be true if the pose monitoring platform 212 only acquires image data generated by the image sensor 210. The image data may initially be analyzed by the pose monitoring platform 212, and then the image data—or analyses of the image data—may be transmitted to the computer server for storage in the digital profile.

The image sensor 210 may be any electronic sensor that is able to detect and convey information in order to generate images, generally in the form of image data (also called "pixel data"). Examples of image sensors include charge-coupled device ("CCD") sensors and complementary metal-oxide semiconductor ("CMOS") sensors. The image sensor 210 may be part of a camera module (or simply "camera") that is implemented in the computing device 200. In some embodiments, the image sensor 210 is one of multiple image sensors implemented in the computing device 200. For example, the image sensor 210 could be included in a front- or rear-facing camera on a mobile phone. In some embodiments, the image sensor may be externally connected to the computing device 200 such that the image sensor 210 generates image data that is representative of a stream of images of an environment and sends the image data to the pose monitoring platform 212.

For convenience, the pose monitoring platform 212 may be referred to as a computer program that resides in the memory 204. However, the pose monitoring platform 212 could be comprised of hardware or firmware in addition to, or instead of, software. In accordance with embodiments described herein, the pose monitoring platform 212 may include a processing module 214, monitoring module 216, analysis module 218 and graphical user interface ("GUI") module 220. These modules can be an integral part of the pose monitoring platform 212. Alternatively, these modules can be logically separate from the pose monitoring platform 212 but operate "alongside" it. Together, these modules may enable the pose monitoring platform 212 to guide a participant through sessions that are performed as a part of a program designed to improve performance of a physical activity or accomplish some other objective, such as manage or treat an MSK condition that is affecting a particular anatomical region.

The processing module 214 can process image data obtained from the image sensor 210 over the course of a session. The image data may be used to infer a spatial position or orientation of one or more anatomical landmarks, and insights into performance of the physical activity can be gained through analysis of the inferred spatial position or orientation. For example, the processing module 214 may perform operations (e.g., filtering noise, changing contrast, reducing size) to ensure that the data can be handled by the other modules of the pose monitoring platform 212. As another example, the processing module 214 may temporally align the data with data obtained from another source (e.g., the sensor units 222A-N or another image sensor) if multiple data are to be used to establish the spatial position or orientation of the anatomical landmarks of interest.

As mentioned above, the processing module 214 may additionally or alternatively process sensor data obtained from sensor units 222A-N attached to the participant proximate to anatomical landmarks of interest over the course of the session. The processing module 214 can parse, filter or otherwise alter this sensor data so that it is usable by the other modules of the pose monitoring platform 212. As an example, in some embodiments, the processing module 214 may examine this sensor data in order to ensure that multiple streams of data received from different components (e.g., Sensor Unit A 222A and Sensor Unit B 222B) are temporally aligned with one another.

Moreover, the processing module 214 may be responsible for processing information input through interfaces generated by the GUI module 220. For example, the GUI module 220 may be configured to generate a series of interfaces that are presented in succession to a participant as she completes physical activities as part of a session. On some or all of these interfaces, the participant may be prompted to provide input. For example, the participant may be requested to indicate (e.g., via a verbal command or tactile command provided via, for example, the display mechanism 206) that she is ready to proceed with the next physical activity, that she completed the last physical activity, that she would like to temporarily pause the session, etc. These inputs can be examined by the processing module 214 before appropriate action (e.g., information being forwarded to another module) is taken.

The monitoring module 216 can monitor ongoing movement of the participant as she completes physical activities as part of a session. While the processing module 214 may be responsible for processing data streamed to the pose monitoring platform 212 (e.g., by the image sensor 210 or, in some embodiments, the sensor units 222A-N), the monitoring module 216 may be responsible for determining whether the participant is moving as would be expected when completing a physical activity. As an example, assume that the imager sensor 210 is positioned in front of a participant. During a session, the participant may be instructed to perform an exercise such as a side plank in which the hips are lifted away from the ground. In such a scenario, the monitoring module 216 can examine image data generated by the image sensor 210 to determine whether the thorax and lumbar regions of the participant's body are moving—either in terms of 3D space or with respect to one another—as would be expected given the exercise.

Figure 2B:
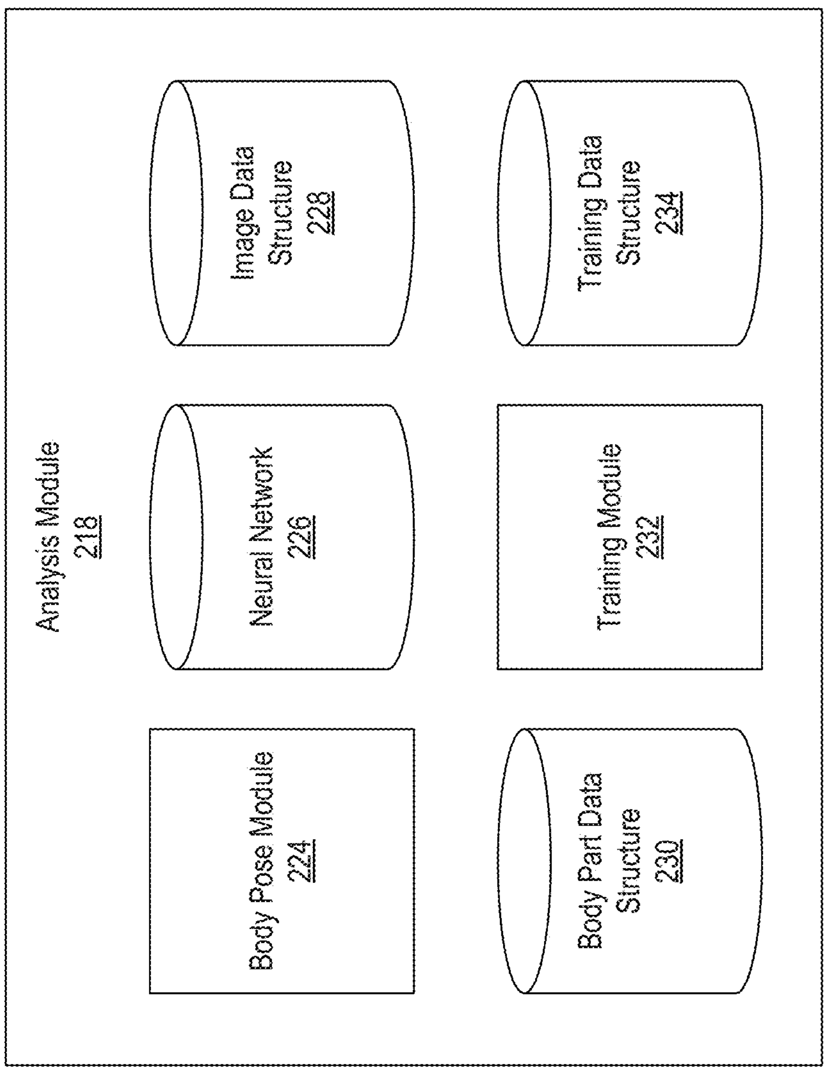
FIG. 2B illustrates an analysis module of the pose monitoring platform of FIG. 2A.

The analysis module 218 may be responsible for determining adherence to individual physical activities, sets of physical activities performed as part of a session, or sets of sessions performed as part of a program. As shown in FIG. 2B, the analysis module 218 can include, or at least be able to access, a body pose module 224, a neural network 226, an image data structure 228, a body part data structure 230 a training module 232, and a training data structure 234. Note that, in some embodiments, the analysis module 218 may include a subset of the modules and data structures shown in FIG. 2B. The analysis module 218 may also include additional modules or data structures that are not shown in FIG. 2B.

The body pose module 224 may be responsible for determining estimated poses of body parts as participants perform physical activities. Body parts may include any portion of a participant's body that is used to perform a physical activity (e.g., hands, feet, torso, etc.). A body part may refer to a single anatomical landmark (e.g., a hand), one anatomical landmark in relation to another anatomical landmark (e.g., a hand in relation to an elbow), or multiple anatomical regions in relation to a single anatomical region (e.g., fingers of a hand in relation to a wrist) or multiple anatomical regions in relation to each other (e.g., a hand, wrist, and elbow in relation to each other). Physical activities may include movements performed for different purposes, including for wellness, sports, dance, virtual reality experiences, augmented reality experiences, physical therapy, or any other activity that requires physical movement. Some examples of physical activities include dance moves (e.g., plies, moonwalks, shuffles, etc.), sporting techniques (e.g., football throws, soccer kicks, tennis serves, basketball layups, yoga poses, etc.), exercises (e.g., planks, hip extensions, etc.), stretches, posture techniques (e.g., standing or sitting at a desk for healthy back and neck), cooking techniques (e.g., chopping, kneading, dicing, etc.), and the like.

The body pose module 224 can obtain, from the image sensor 210, image data of an environment that includes a participant performing one or more physical activities. In some embodiments, the image data may depict the participant's entire body in the environment. In other embodiments, the image data may depict one or more of the participant's body parts in the environment. For example, the image data may only depict the hands or feet of the participant. In some embodiments, the image data may depict one or more body parts of multiple participants. Assume, for example, that the computing device 200 is arranged such that most of, if not all, of a room (e.g., a dance studio) is visible to the image sensor 210. In such a scenario, multiple participants performing a physical activity (e.g., dancing) may be captured in the image data, though different body parts of each participant may be visible in the image data. The body pose module 224 may store the image data in the image data structure 228 along with an indication of a time, date, or location associated with the capture of the image data.

In some embodiments, the image data structure 228 may be implemented on a computing device 200—and more specifically, in the memory 204—where the image sensor 210 is located. In other embodiments, the image data structure 228 may be external to the computing device 200. For example, the image data structure 228 may be implemented in a server system (e.g., server system 110 of FIG. 1) that is accessible to the computing device 200 via the communication module 208. The image data structure 228 may be formatted to expedite pose analysis by the analysis module 218. For example, in some instances, the image data structure 228 may be tabulated by identifiers associated with the image sensor 210 that generates the image data, identifiers of the participants depicted in or otherwise associated with the image data, and/or identifiers of the computing device 200 on which the analysis module 218 executes or from which the image data is transmitted to the analysis module 218.

The body pose module 224 can extract one or more feature maps from the image data. In one embodiment, the body pose module 224 segments the image data into contiguous regions of pixels. At a high level, the image data may be of a scene that includes the participant performing a physical activity in an environment, and therefore each contiguous region of pixels may be associated with a portion of the scene. In some embodiments, the body pose module 224 segments the image data based on objects shown in the image data. For example, the body pose module 224 may extract pixels representing the floor into a first region, a piece of furniture into a second region, a participant's right hand into a third region, etc. In another embodiment, the body pose module 224 segments the image data based on contrast between colors of or distance between the pixels. The body pose module 224 may use one or more machine learning models to segment the image data or may use an algorithm (e.g., one designed for edge-, threshold-, region-, or cluster-based segmentation). For example, pixels representing a hand may have similar coloring and be within a set distance threshold of one another compared to pixels of a green wall behind the hand. The body pose module 224 may create groups of pixels, each associated with a single color or range of colors (e.g., light to dark green, dark yellow to light orange, dark blue to dark purple). For each group, the body pose module 224 may determine a weighted average location of the pixels and remove pixels from the group that are a threshold distance away from the weighted average location. The body pose module 224 may iterate upon this grouping process until every pixel is associated with a group (e.g., a segment of the image data).

The body pose module 224 can extract a feature map for each segment of the image data. The term "feature map" may be used to refer to a vectorial representation of features in the image data. Said another way, each "feature map" may be a vectorial representation of content in the corresponding segment of the image data. In neural networks, a feature map is usually the output of a convolutional layer that represents specific features in the input—here, an image. A feature map is generally not intuitively meaningful for humans, but instead may be abstract representations of the input that is useful for the task at hand. The dimensions of the feature map may be based on the input, neural network, or task at hand. Here, for example, the body pose module 224 may extract feature maps having predetermined dimensions (e.g., 32×32×128) by applying a filter or feature detector to each segment. For example, the body pose module 224 may apply a filter that detects skin to a segment and may receive, as output, a feature map that identifies which portions of the segment include skin. The body pose module 224 may store the segments and associated feature maps in the image data structure 228 or another datastore.

The body pose module 224 can apply the neural network 226 to each feature map. Note that, in some embodiments, the neural network 226 could be applied directly to each segment of the image rather than the corresponding feature maps. The neural network 226 may include a series of convolutional layers and a series of connected layers of decreasing size, and the last layer of the neural network 226 may be a sigmoid activation function. The neural network 226 can include a plurality of parallel branches that are configured to together estimate poses of body parts based on the feature maps. A first branch of the neural network 226 could be configured to determine a likelihood that the portion of the environment associated with the segment includes a body part, while a second branch of the neural network 226 could be configured to determine an estimated pose of the body part in the portion of the environment associated with the segment. In some embodiments, the body pose module 224 may employ an additional machine learning framework or alternative machine learning framework to the neural network 226 to estimate poses of body parts.

In some embodiments, the neural network 226 includes additional or alternative branches that the body pose module 224 employs to determine a pose of a body part. For example, the neural network 226 may include a set of branches corresponding to different body parts. In some embodiments, this set of branches is selected so as to cover all body parts that could possibly be included in the segment. Accordingly, the neural network 226 may include a set of hand branches that determine a likelihood that the segment includes a hand and estimated poses of hands in the segment. The neural network may similarly include a set of branches that detect right legs in the segment and determine poses of the right legs in the segment and another set of branches that detects and determines poses of left legs in the segment. Further, the neural network 226 may include branches for other anatomical landmarks (e.g., elbows, fingers, neck, torso, upper body, hip to toes, chest and above, etc.) and/or sides of a participant's body (e.g., left, right, front, back, top, bottom). Accordingly, the first branch of the neural network 226 could be part of a set of branches, each of which is associated with a different body part and is independently appliable. Similarly, the second branch of the neural network 226 could be part of a set of branches, each of which is associated with a different pose and is independent appliable. The neural network 226 is further described below in relation to the training module 232.

The body pose module 224 can compare the likelihood determined by the first branch of the neural network 226 to a threshold value. The higher the likelihood, the more likely that the feature map includes a body part associated with the first branch of the neural network 226. In some embodiments, if the body pose module 224 determines that the likelihood is greater than the threshold value, the body pose module 224 stores an indication in the body part data structure 230 that the body part in the segment is in the estimated pose determined by the second branch of the neural network 226. In embodiments where the neural network 226 includes a set of branches, each corresponding to a different body part (e.g., such as each body part of the body or a subset of body parts related to a specific portion of the body, such as the torso, lower body, etc.), the body pose module 224 can compare the likelihood determined by the set to a threshold related to the body part of the set. If the likelihood exceeds the threshold, the body pose module 224 can store an indication in the body part data structure 230 that the body part in the segment is in the estimated pose determined by the set. In some embodiments, the body pose module 224 stores the indication with the time, date, and or location associated with the image data of the segment.

In some embodiments, for each indication, the body pose module 224 may cause the display mechanism 206 to display an indication that the participant is performing the estimated pose with the body part. The body pose module 224 may do so in near real time. For example, the body pose module 224 may receive and segment image data and apply the neural network 226 to determine a pose of a body part as the participant is performing a physical activity in real time. After performing such processing, the body pose module 224 may cause the display mechanism 206 to display the indication, allowing the participant to move her body parts if she is intending to be in a different pose. In some embodiments, the body pose module 224 may send indications to the GUI module 220 for display via the display mechanism 206, rather than directly causing the display mechanism 206 to display indications or other information.

For each indication, the body pose module 224 can determine one or more physical activities associated with estimated pose. For instance, the body pose module 224 may access physical activities related to poses in the body part data structure 230. For example, the pose "left-handed fist" may be associated with the physical activities "kickboxing jab," "volleyball serve," "hand therapy fist," and "cooking utensil hold." The body pose module 224 may access data (e.g., image data generated by the image sensor 210 or sensor data generated by the sensor units 222A-N) associated with the participant. As noted above, this data could be retrieved from the memory 204 or acquired from a source external to the computing device 200 via the communication module 208. The body pose module 224 can select a physical activity from among the physical activities associated with the pose based on the participant's data. For example, if the participant's data indicates that she is undergoing therapy for her hand, the body pose module 224 may select the physical activity "hand therapy fist." The body pose module 224 may cause the display mechanism 206 to display an indication of the physical activity to the participant. In further embodiments, the body pose module 224 may access instructions for how the participant could improve her technique (e.g., to achieve a therapeutic goal) for the physical activity based on the pose from the body part data structure 230 and cause the display mechanism 206 to display the instructions to the participant. For example, if the body pose module 224 determines that, while kickboxing, the participant is posing her hand in a fist with her thumb enclosed by her fingers, the body pose module 224 may cause the display mechanism 206 to display instructions for the participant move her thumb to rest on the outside of her fingers.

In some embodiments, the body pose module 224 can determine whether a physical activity was successfully completed by the participant based on estimated body poses. For example, if an estimated body pose does not match the physical activity that a participant is supposed to be doing (e.g., determined based on participant's data), then the body pose module 224 may prevent further progression through a session hosted by the pose monitoring platform 212 until the physical activity is determined to have been performed with one or more predetermined poses. In another example, the body pose module 224 may update the session based on the estimated body pose to further teach the participant how to perform the body pose if the participant has not matched a pattern representative of a first physical activity. The body pose module 224 may also update the session to focus on a second physical activity upon determining that the body pose does match the pattern.

The training module 232 can train a first branch (or a first set of branches, each of which is able to independently determine a separate likelihood of a separate body part) of the neural network 226 to determine whether image data contains body parts. The training module 232 may obtain a set of images from the pose monitoring platform 212 or from another computing device that is communicatively connected to the pose monitoring platform 212. The training module 232 can determine, based on the 2D or 3D locations of the body parts in the set of images, spatial positions of the body parts at corresponding points in time. In one embodiment, the training module 232 may use a machine learning model trained for object detection (also called an "object detection model" or "object detector"), a machine learning model trained for object recognition (also called an "object recognition model" or "object recognizer"), or another type of machine learning model or computer vision technique to determine spatial positions of body parts. For each body part detected in the set of images, the training module 232 can place a bounding box around that body part in each image. The training module 232 can then iteratively displace the bounding box within the bounds of the image until the bounding box no longer surrounds spatial positions associated with the body part. For each displaced instance of the bounding box, the training module 232 can add the portion of the image associated with (e.g., enclosed by) the bounding box to a first training dataset that is stored in the training data structure 234. The training module 232 can then train the first branch (or the first set of branches) on the first training dataset.

In some embodiments, the training module 232 causes a display mechanism 206 of a computing device 200 to display each digital image in the set. The training module 232 may receive input indicative of interactions (e.g., made through the display mechanism 206 or another control mechanism), where one or more of the interactions indicate placement of bounding boxes around body parts in the images and includes labels for the bounding boxes with poses of an included body part. The training module 232 can add the portion of the image associated with each bounding box to a second training dataset in the training data structure 234. The training module 232 can then train the second branch of the neural network 226 on the second training dataset. In embodiments where the neural network includes a set of branches for each body part, the training module 232 can train the branches configured to estimate a pose of the body part on the second training dataset.

The training module 232 can train the neural network 226 on the training data. In some embodiments, the training module 232 may retrain the neural network 226 each time that new images are added to the first training dataset or second training dataset. In other embodiments, the training module 232 may retrain the neural network 226 in response to a determination that at least a predetermined number of new images have been added to the first training dataset or second training dataset. In further embodiments, the training module 232 may separate the data to be used for training based on the body part shown in each bounding box and train branches of the neural network 226 on training data corresponding to a particular body part (e.g., the branch trained for recognizing the pose of a foot is trained on images of feet, the branch trained for recognizing the pose of a hand is trained on images of hands, etc.).

Figure 2C:
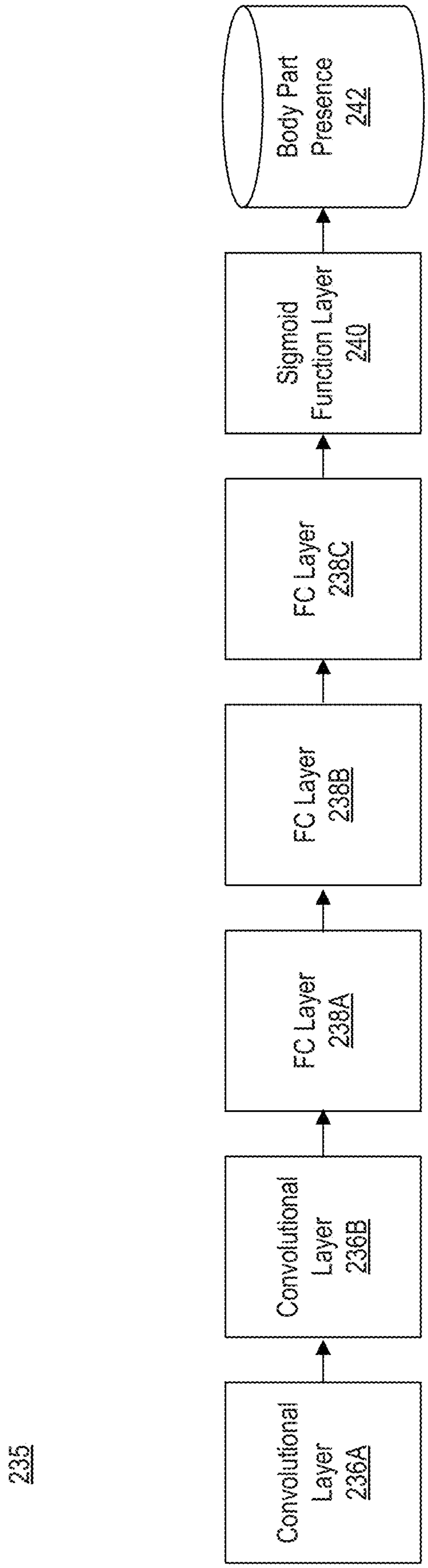
FIG. 2C illustrates a block diagram of layers of a branch of the neural network of FIG. 2B.

FIG. 2C illustrates a block diagram of layers of the first branch 235 (e.g., the body part detection branch) of the neural network 226 of FIG. 2B. The first branch 235 can include a first convolutional layer 236A followed by a second convolutional layer 236B. The convolutional layers are followed by three fully connected ("FC") layers 238A-C and a sigmoid function layer 240 that can employ the sigmoid activation function. After employing the sigmoid activation function, the first branch 235 can produce, as output, an indication 242 of whether one or more body parts are present in an image provided as input. In some embodiments, the first branch 235 may include any number of the different types (e.g., convolutional, FC, etc.) layers shown in FIG. 2C. At a high level, the main difference between the first branch 235 and a second branch (not shown) of the neural network 226 is that the second branch is designed to estimate pose. Accordingly, the second branch may contain many more convolutional layers arranged in multiple sequential stages (e.g., three stages, five stages, seven stages). Assume, for example, that the second branch contains three sequential stages. The first and second stages may each include five convolutional layers, while the third stage may have fourteen convolutional layers and three FC layers. The second branch may not contain any sigmoid layer at the end. Accordingly, the second branch is "heavier" from a computational perspective given the higher complexity of its task, as it may be responsible for estimating the entire pose of a given body part rather than a single presence value.

Figure 3A:
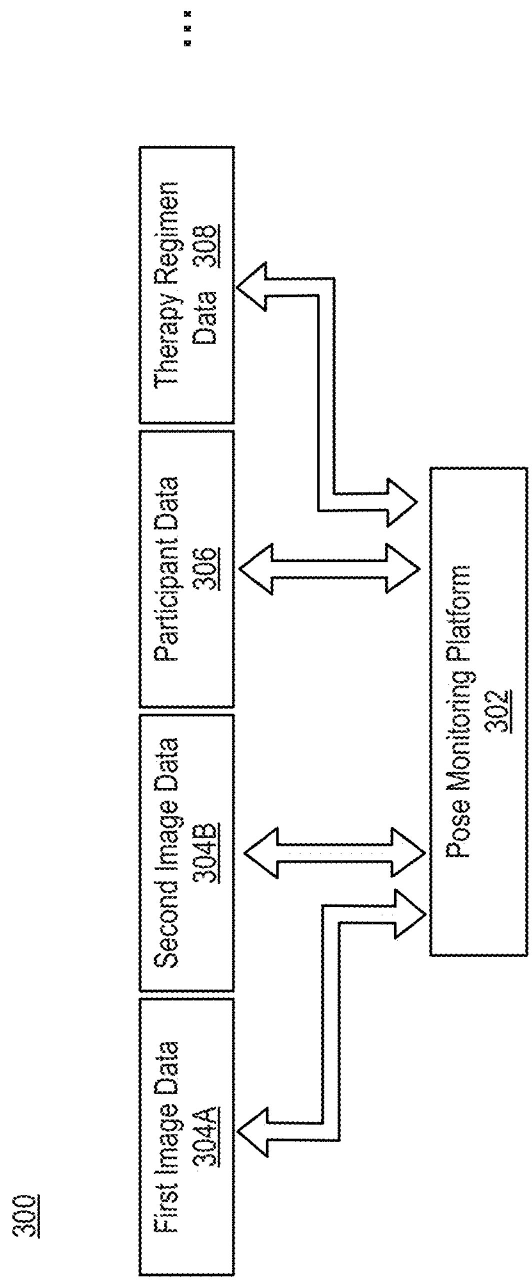
FIG. 3A depicts an example of a communication environment that includes a pose monitoring platform configured to receive several types of data.

FIG. 3A depicts an example of a communication environment 300 that includes a pose monitoring platform 302 configured to receive several types of data. Here, for example, the pose monitoring platform 302 receives first image data 304A that captured by a first image sensor (e.g., image sensor 210 of FIG. 2A that captures a front view of a participant) located in front of a participant, second image data 304B generated by a second image sensor (e.g., that captures a rear or side view of the participant), participant data 306 (also called "patient data" or "user data") that is representative of information regarding the participant, and therapy regimen data 308 that is representative of information regarding the program in which the participant is enrolled. Those skilled in the art will recognize that these types of data have been selected for the purpose of illustration. Other types of data, such as community data (e.g., information regarding characteristics and adherence of cohorts of participants), could also be obtained by the pose monitoring platform 302.

These data may be obtained from multiple sources. For example, the therapy regimen data 308 may be obtained from a network-accessible server system managed by a digital service that is responsible for enrolling and then engaging participants in programs. The digital service may be responsible for defining the series of physical activities to be performed during sessions based on input provided by coaches. As another example, the participant data 306 may be obtained from various computing devices. For instance, some participant data 306 may be obtained directly from participants (e.g., who input such data during a registration procedure or during a session), while other participant data 306 may be obtained from employers (e.g., who are promoting or facilitating a wellness program) or healthcare facilities such as hospitals and clinics. Additionally or alternatively, participant data 306 could be obtained from another computer program that is executing on, or accessible to, the computing device on which the pose monitoring platform 302 resides. For example, the pose monitoring platform 302 may retrieve participant data 306 from a computer program that is associated with a healthcare system through which the participant receives treatment. As another example, the pose monitoring platform 302 may retrieve participant data 306 from a computer program that establishes, tracks, or monitors the health of the participant (e.g., by measuring steps taken, calories consumed, heart rate, blood pressure, blood glucose level, etc.).

Figure 3B:
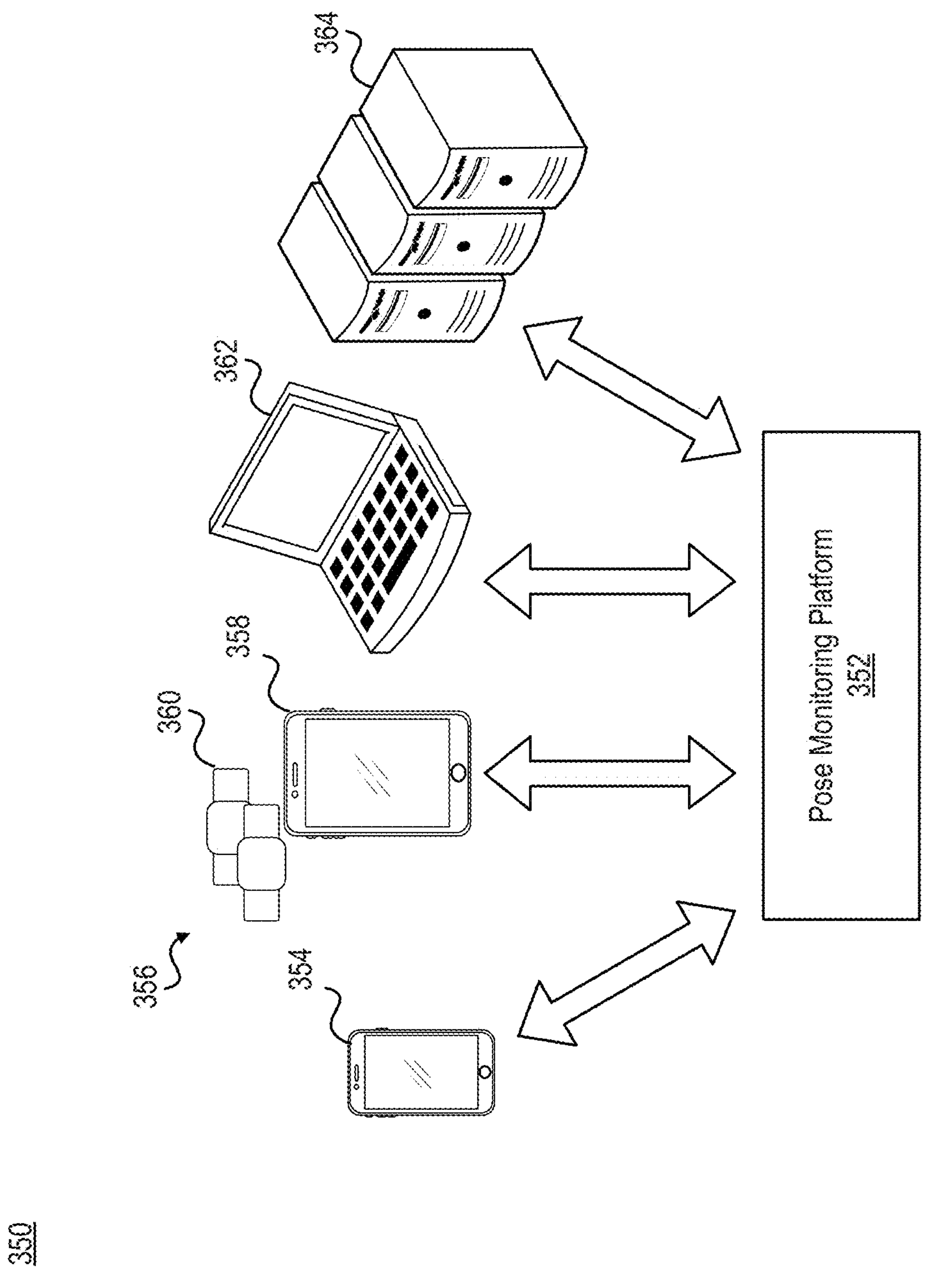
FIG. 3B depicts another example of a communication environment that includes a pose monitoring platform that is communicatively connectable to, and therefore able to obtain data from, different sources.

FIG. 3B depicts another example of a communication environment 350 that includes a pose monitoring platform 352 that is communicatively connectable to, and therefore able to obtain data from, different sources. For example, the pose monitoring platform 352 may be able to obtain data from a mobile phone 354, a therapy system 356 comprised of a tablet computer 358 and one or more sensor units 360 (e.g., image sensors), a personal computer 362, or a network-accessible server system 364 (collectively referred to as the "networked devices"). For example, the pose monitoring platform 352 may obtain image data—from which movement of a participant while performing a physical activity is determinable—from the mobile phone 354. As another example, the pose monitoring platform 352 may obtain sensor data—from which movement of a participant while performing a physical activity is determinable—from the therapy system 356. Other data (e.g., therapy regimen information, models of exercise-induced movements, feedback from coaches, and processing operations) could be obtained from the personal computer 362 or network-accessible server system 364.

The networked devices can be connected to the pose monitoring platform 352 via one or more networks. These networks can include PANs, LANs, WANs, MANs, cellular networks, the Internet, etc. Additionally or alternatively, the networked devices may communicate with one another over a short-range wireless connectivity technology. For example, if the pose monitoring platform 352 resides on the mobile phone, data generated by the mobile phone—like image data generated by its image sensor—may not need to traverse any networks; however, data could be obtained from the network-accessible server system 364 over the Internet via a Wi-Fi communication channel. As another example, if the pose monitoring platform 352 resides on the tablet computer 358, data may be obtained from the sensor units 360 over a Bluetooth communication channel, while data may be obtained from the network-accessible server system 364 over the Internet via a Wi-Fi communication channel.

Embodiments of the communication environment 350 may include a subset of the networked devices. For example, some embodiments of the communication environment 350 include a pose monitoring platform 352 that resides on the mobile phone 354 and monitors pose in real time based solely on analysis of image data generated by the mobile phone 354. As another example, some embodiments of the communication environment 350 include a pose monitoring platform 352 that obtains data from the therapy system 356 (and, more specifically, from the sensor units 360) in real time as physical activities as performed during a session and additional data from the network-accessible server system 362. This additional data may be obtained periodically (e.g., on a daily or weekly basis, or when a session is initiated).

Approaches to Estimating Pose

Figure 4A:
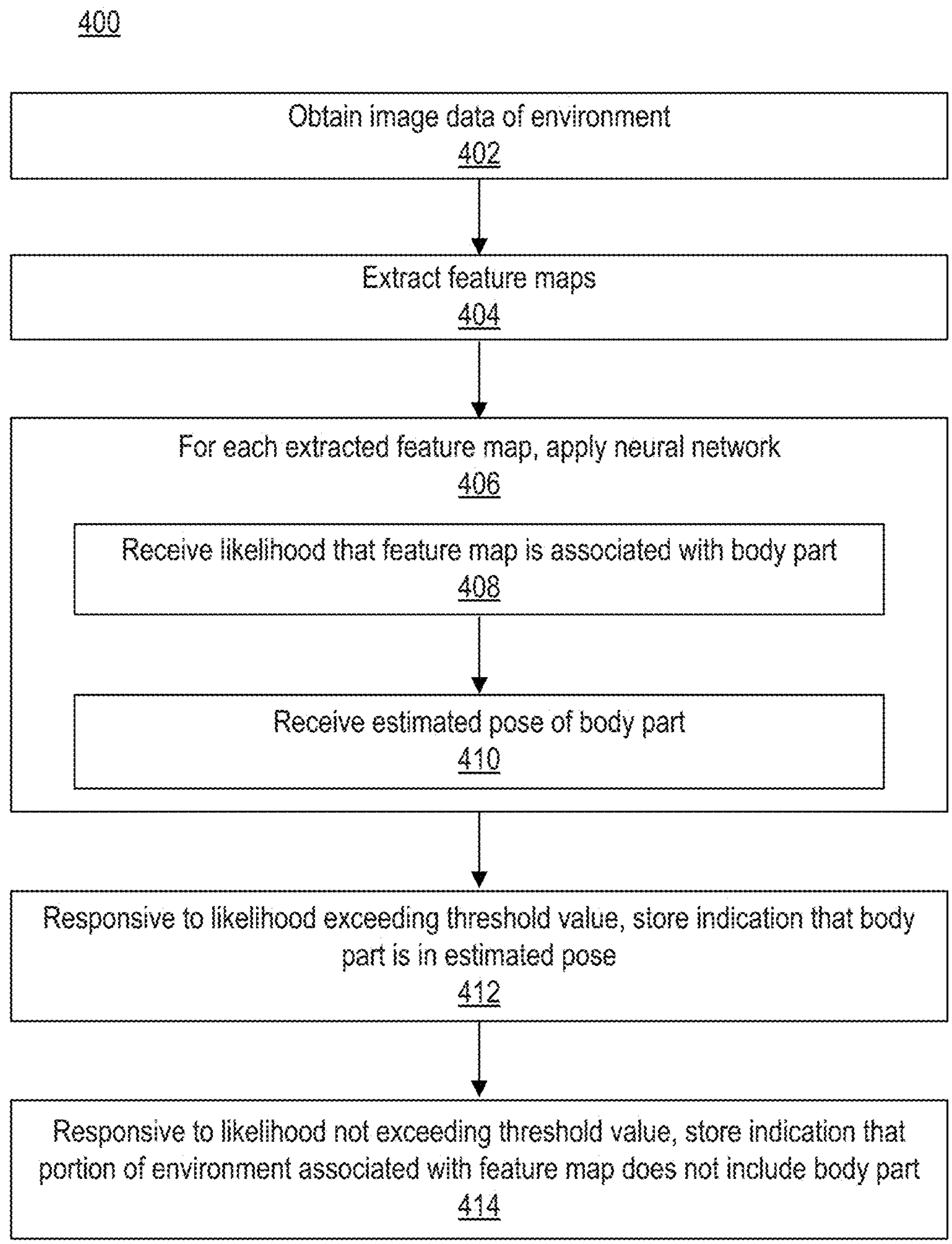
FIG. 4A depicts a flow diagram of a process for determining an estimated pose of a body part.

FIG. 4A depicts a flow diagram 400 of a process for determining an estimated pose of a body part. Initially, the body pose module 224 can obtain an image of an environment (step 402). The image could be generated by the same computing device on which the body pose module 224 executes, or the image could be generated by another computing device. Accordingly, the body pose module 224 may acquire the image directly from the image sensor 210 in some embodiments, while in other embodiments the body pose module 224 may acquire the image from a datastore (e.g., the image data structure 228 of FIG. 2 or the server system 110 of FIG. 1). The body pose module 224 can segment the image into a plurality of segments, each of which may be representative of a contiguous region of pixels that is associated with a portion of the environment. Then, the body pose module 224 can extract feature maps from the segments (step 404). For each extracted feature map, the body pose module 224 can apply the neural network 226 to the extracted feature map (step 406). The neural network 226 may comprise a series of convolutional layers and a series of connected layers of decreasing size. In some embodiments, the last layer of the neural network 226 is a sigmoid activation function.

In applying the neural network 224 to an extracted feature map, the body pose module 224 can receive, from a first branch of the neural network 226, a likelihood that the portion of the environment associated with the extracted feature map includes a given body part (step 408). As discussed above, the first branch of the neural network 226 may be trained to detect digital features that are representative of the given body part. The body pose module 224 can receive, from a second branch of the neural network 226, an estimated pose of the given body part in the portion of the environment associated with the extracted feature map (step 410). Thereafter, the body pose module 224 can compare the likelihood to a threshold value that is programmed in the memory 204 of the computing device 200 and accessible to the pose monitoring platform 212. Responsive to determining that the likelihood exceeds the threshold value, the body pose module 224 can store, in the body part data structure 230, an indication that the given body part located in the portion of the environment is in the estimated pose (step 412). Responsive to determining that the likelihood does not exceed the threshold value, the body pose module 224 can store an indication that the segment does not include a body part in association with the segment in the image data structure 228 (step 414). For example, the body pose module 224 may store the digital image in relation to a time and, for each segment, an indicator of whether that segment includes the given body part and a pose of the given body part.

The process 400 may include additional or alternative steps to those shown in FIG. 4A. For example, in some embodiments, the body pose module 224 is able to programmatically associate the estimated pose of the given body part with the portion of the environment at a given point in time (e.g., when the image data was captured, or when the neural network 226 output the estimated pose, etc.).

In some embodiments, the body pose module 224 determines, based on the estimated pose, a physical activity being performed by an individual to whom the given body part belongs. As discussed above, the individual may be referred to as a "participant" that engages in a physical activity while being monitored. The body pose module 224 may cause presentation of an interface at the display mechanism 206 to display an indication identifying the estimated pose or the physical activity. In further embodiments, the body pose module 224 may determine, based on the estimated pose, one or more instructions for improving a technique associated with the estimated pose. For example, the body pose module 224 may access a series of body poses associated with the physical activity being performed and a series of body poses that are visually similar to one another (e.g., based on input from an external operator or based on a comparison of pixel locations of images of the body poses). The body pose module 224 may select a body pose associated with the estimated pose and the physical activity as the body pose that the participant may have been trying to accomplish and generate instructions of how to form the selected body pose. The body pose module 224 may cause the interface presented on the display mechanism 206 to display the instructions to the participant.

In some embodiments, the training module 232 receives a set of images and determines, based on locations in the set of images, spatial positions of one or more body parts in the set of digital images. Assume, for example, that the neural network 226 is trained to identify the presence and location of a left hand, right hand, or hands more generally. For each hand in the set of images, the training module 232 can place a bounding box around the hand and then iteratively displace the bounding box until the bounding box does not include spatial positions of one or more hands. For each displaced instance of the bounding box, the training module 232 can add a portion of the set of digital images associated with the displaced bounding box to a training dataset. The training module 232 may train the first branch of the neural network 226 on the training dataset.

Figure 4B:
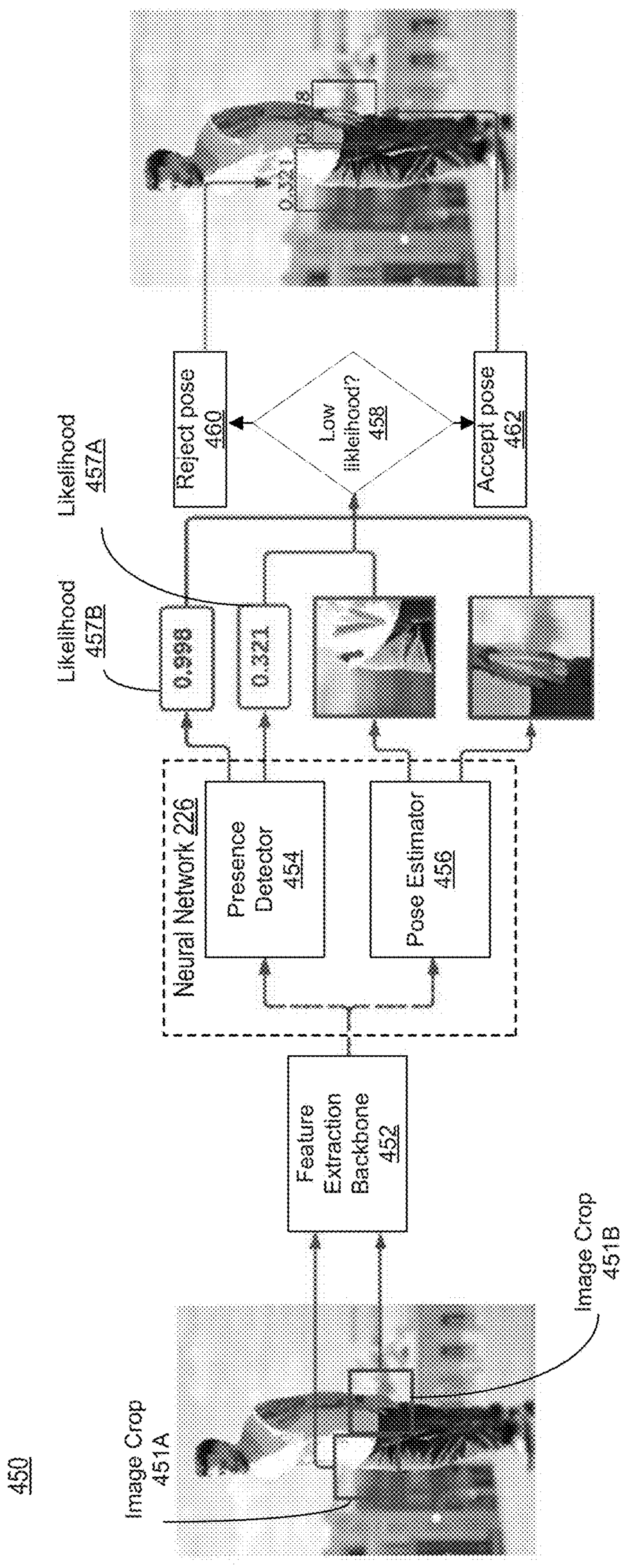
FIG. 4B depicts a flow diagram of a process for accepting an estimated pose of a body part.

FIG. 4B depicts a flow diagram of a process 450 for accepting an estimated pose of a body part. In this example, the pose monitoring platform 212 is configured to determine poses of hands in images. Here, the body pose module 224 segments an input image into two image crops 451A-B. Specifically, the body pose module 224 segments the input image into a first image crop 451A corresponding to a right hand and a second image crop 451B corresponding to a left hand. In some embodiments, the neural network 226 is trained to distinguish between left and right hands, while in other embodiments, the neural network 226 is not trained to distinguish between left and right hands. The body pose module 224 may apply a feature extraction backbone 452 to independently extract a feature map for each image crop 451A-B. The body pose module 224 can then input each image crop 451A-B into the neural network 226. The neural network 226 can comprise a presence detector 454 (e.g., that is representative of the first branch) and a pose estimator 456 (e.g., that is representative of the second branch). The presence detector 454 can output likelihoods 457A-B that the image crops 451A-B include a hand. For each image crop 451A-B, the presence detector 454 can independently compute, infer, or otherwise determine the corresponding likelihood 457A-B. Here, for example, the presence detector 454 determines a low likelihood 457A of 0.321 for the first image crop 451A and a high likelihood 457B of 0.998 for the second image crop 451B. The pose estimator 456 can output estimated poses of each hand in the image crops 451A-B. The estimated poses may be indications of specific poses, feature vectors representing the poses, or any other representation of an estimated pose. The body pose module 224 can then whether the likelihood is low (e.g., by determining that the likelihood is below a predetermined threshold) or high (e.g., by determining that the likelihood is above the predetermined threshold). The body pose module 224 can reject 460 the corresponding estimated pose if the likelihood is determined to be low, like in the case of image crop 451A. If the likelihood is determined to be high, the body pose module 224 can accept 462 the corresponding estimated pose, like in the case of image crop 451B.

Processing System

Figure 5:
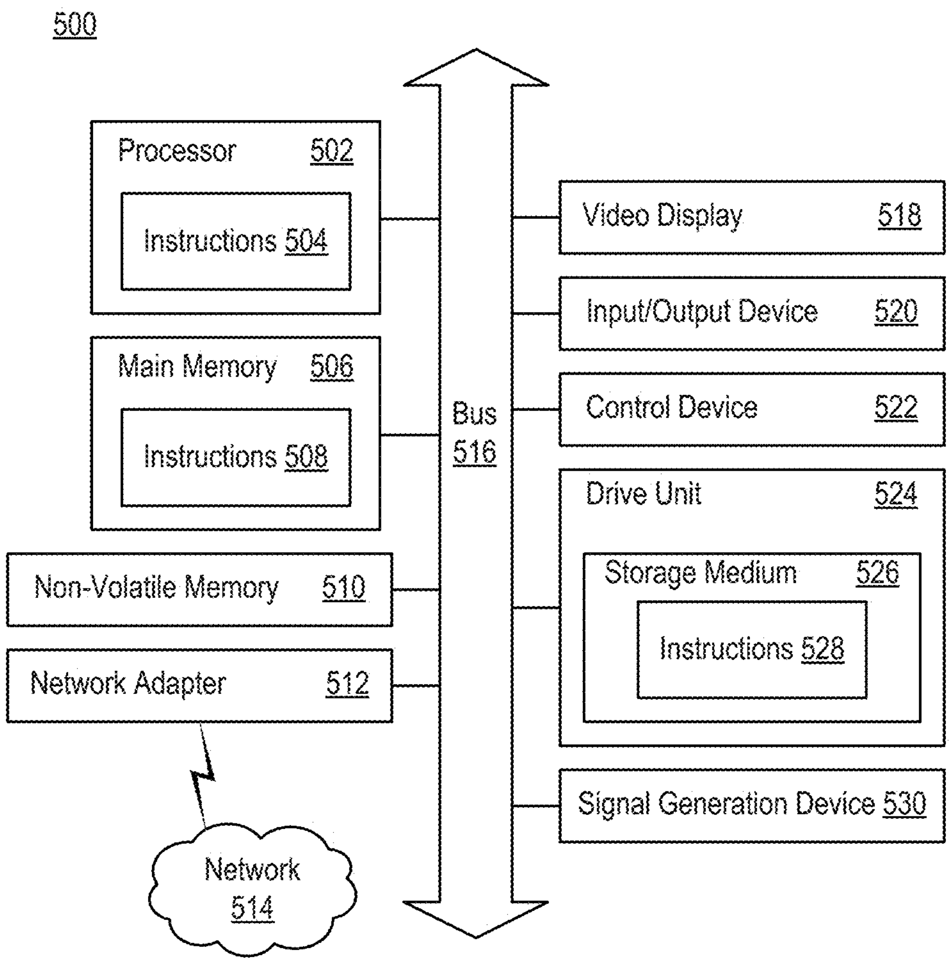
FIG. 5 is a block diagram illustrating an example of a processing system in which at least some operations described herein can be implemented.

FIG. 5 includes a block diagram illustrating an example of a processing system 500 in which at least some operations described herein can be implemented. For example, components of the processing system 500 may be hosted on a computing device that includes a motion monitoring platform (e.g., motion monitoring platform 102 of FIG. 1 or motion monitoring platform 212 of FIG. 2).

The processing system 500 can include a processor 502, main memory 506, non-volatile memory 510, network adapter 512, video display 518, input/output devices 520, control device 522 (e.g., a keyboard or pointing device such as a computer mouse or trackpad), drive unit 524 including a storage medium 526, and signal generation device 530 that are communicatively connected to a bus 516. The bus 516 is illustrated as an abstraction that represents one or more physical buses or point-to-point connections that are connected by appropriate bridges, adapters, or controllers. The bus 516, therefore, can include a system bus, a Peripheral Component Interconnect ("PCI") bus or PCI-Express bus, a HyperTransport ("HT") bus, an Industry Standard Architecture ("ISA") bus, a Small Computer System Interface ("SCSI") bus, a Universal Serial Bus ("USB") data interface, an Inter-Integrated Circuit ("$I^2C$") bus, or a high-performance serial bus developed in accordance with Institute of Electrical and Electronics Engineers ("IEEE") 1394.

While the main memory 506, non-volatile memory 510, and storage medium 526 are shown to be a single medium, the terms "machine-readable medium" and "storage medium" should be taken to include a single medium or multiple media (e.g., a centralized/distributed database and/or associated caches and servers) that store one or more sets of instructions 528. The terms "machine-readable medium" and "storage medium" shall also be taken to include any medium that is capable of storing, encoding, or carrying a set of instructions for execution by the processing system 500.

In general, the routines executed to implement the embodiments of the disclosure can be implemented as part of an operating system or a specific application, component, program, object, module, or sequence of instructions (collectively referred to as "computer programs"). The computer programs typically comprise one or more instructions (e.g., instructions 504, 508, 528) set at various times in various memory and storage devices in a computing device. When read and executed by the processors 502, the instruction(s) cause the processing system 500 to perform operations to execute elements involving the various aspects of the present disclosure.

Further examples of machine- and computer-readable media include recordable-type media, such as volatile memory devices and non-volatile memory devices 510, removable disks, hard disk drives, and optical disks (e.g., Compact Disk Read-Only Memory ("CD-ROMs") and Digital Versatile Disks ("DVDs")), and transmission-type media, such as digital and analog communication links.

The network adapter 512 enables the processing system 500 to mediate data in a network 514 with an entity that is external to the processing system 500 through any communication protocol supported by the processing system 500 and the external entity. The network adapter 512 can include a network adaptor card, a wireless network interface card, a router, an access point, a wireless router, a switch, a multilayer switch, a protocol converter, a gateway, a bridge, bridge router, a hub, a digital media receiver, a repeater, or any combination thereof.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments can vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method performed by a computer program executed on a computing device, the method comprising:

receiving multiple digital images;

determining locations of one or more anatomical landmarks in each of the multiple digital images;

determining, based on the locations, spatial positions of one or more hands in each of the multiple digital images;

for each hand determined to be in one of the multiple digital images, placing a bounding box around the hand, and iteratively displacing the bounding box until the bounding box does not include the spatial positions of the one or more hands;

for each displaced bounding box, adding a portion of the multiple digital images that is associated with the displaced bounding box to a training dataset;

training a first branch of a neural network on the training dataset;

receiving a digital image of a scene that includes an individual performing a physical activity in an environment;

segmenting the digital image into multiple segments, each of which is representative of a contiguous region of pixels that is associated with a portion of the scene;

for each of the multiple segments, extracting a feature map so as to produce multiple feature maps, each of which is a vectorial representation of content in a corresponding one of the multiple segments; and for each of the multiple feature maps, applying the neural network so as to:

determine, via the first branch of the neural network, a likelihood that the corresponding one of the multiple segments includes a hand, and determine, via a second branch of the neural network, an estimated pose of the hand in the corresponding one of the multiple segments;

comparing the likelihood to a threshold value programmed in memory of the computing device; and responsive to a determination that the likelihood exceeds the threshold value, storing an indication that the hand is in the estimated pose.

2. The method of claim 1, wherein the indication is stored in a data structure that is in the memory of the computing device.

3. The method of claim 1, wherein said storing comprises:

programmatically associating the estimated pose of the hand with the portion of the scene at a given point in time.

4. The method of claim 1, further comprising:

determining, based on the estimated pose, a therapeutic activity being performed by the individual to whom the hand belongs; and displaying, via a graphic user interface on the computing device, an indication of the therapeutic activity.

5. The method of claim 1, further comprising:

determining, based on the estimated pose, an instruction for improving a technique associated with the estimated pose; and displaying, via a graphic user interface on the computing device, the instruction.

6. The method of claim 1, wherein the neural network comprises a series of convolutional layers and a series of connected layers of decreasing size.

7. The method of claim 6, wherein a last layer of the neural network is a sigmoid activation function.

8. The method of claim 1, wherein the digital image is generated by an image sensor included in the computing device, and wherein said segmenting, said extracting, said applying, said comparing, and said storing are performed in real time with the generation of the digital image.

9. The method of claim 1, wherein the digital image includes an individual performing a physical activity, and wherein the method further comprises:

accessing a series of poses that are associated with the physical activity;

establishing feedback based on a comparison of the estimated pose to the series of poses; and causing display of the feedback, so as to indicate to the individual how to improve performance of the physical activity.

10. The method of claim 1, wherein said segmenting comprises:

applying, to the digital image, a machine learning model to generate the multiple segments.

11. The method of claim 1, wherein said segmenting comprises:

providing the digital image to an algorithm that produces or identifies the multiple segments as output.

12. The method of claim 11, wherein the algorithm is designed for edge-, threshold-, region-, or cluster-based segmentation.

13. The method of claim 11, wherein boundaries of the multiple segments are determined by the algorithm through an analysis of color contrast of pixels in the digital image.

* * * * *